United States Patent
Shaaban et al.

(10) Patent No.: US 11,999,708 B1
(45) Date of Patent: Jun. 4, 2024

(54) THIAZOLE TETHERED ORGANOSELENIDES AS 5-LIPOXYGENASE INHIBITORS

(71) Applicant: KING FAISAL UNIVERSITY, Al-Ahsa (SA)

(72) Inventors: Saad Shaaban, Al-Ahsa (SA); Hussein Ba-Ghazal, Al-Ahsa (SA); Mohamed Alaa Mohamed, Al-Ahsa (SA); Abeer M. Ashmawy, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/590,133

(22) Filed: Feb. 28, 2024

(51) Int. Cl.
  *C07D 277/34* (2006.01)
  *A61K 31/427* (2006.01)

(52) U.S. Cl.
  CPC .......... *C07D 277/34* (2013.01); *A61K 31/427* (2013.01)

(58) Field of Classification Search
  CPC ........................... C07D 277/34; A61K 31/427
  See application file for complete search history.

(56) References Cited

FOREIGN PATENT DOCUMENTS

WO   2015058868 A1   4/2015

OTHER PUBLICATIONS

PubChem CID 650872, Jun. 4, 2005.
Heeren M. Gordhan et al, "Evaluation of substituted ebselen derivatives as potential trypanocidal agents"; Bioorg Med Chem Lett. Feb. 1, 2017; 27(3): 537-541. Published online Dec. 10, 2016. doi: 10.1016/j.bmcl.2016.12.021 but no ROS, cancer, ect.
Ewelina Węglarz-Tomczak et al, "Identification of methionine aminopeptidase 2 as a molecular target of the organoselenium drug ebselen and its derivatives/analogues: Synthesis, inhibitory activity and molecular modeling study"; Bioorganic & Medicinal Chemistry Letters vol. 26, Issue 21, Nov. 1, 2016, pp. 5254-5259.
Liang Zhang et al, "Induction of Apoptosis in Human Multiple Myeloma Cell Lines by Ebselen via Enhancing the Endogenous Reactive Oxygen Species Production"; Biomed Res Int. 2014; 2014: 696107. Published online Jan. 27, 2014. doi: 10.1155/2014/696107.
Tianfeng Chen et al, "Mitochondria-mediated apoptosis in human breast carcinoma MCF-7 cells induced by a novel selenadiazole derivative"; Biomedicine & Pharmacotherapy vol. 62, Issue 2, Feb. 2008, pp. 77-84.
Chengfeng Yang et al, "Ebselen Induces Apoptosis in HepG2 Cells through Rapid Depletion of Intracellular Thiols"; Mar. 2000Archives of Biochemistry and Biophysics 374(2): 142-52 DOI:10.1006/abbi.1999.1574.
Dominika Radomska et al, "Selenium Compounds as Novel Potential Anticancer Agents"; Int J Mol Sci. Feb. 2021; 22 (3): 1009. Published online Jan. 20, 2021. doi: 10.3390/ijms22031009.
L González-Santiago et al, "Aplidin® induces JNK-dependent apoptosis in human breast cancer cells via alteration of glutathione homeostasis, Rac1 GTPase activation, and MKP-1 phosphatase downregulation"; Cell Death Differ 13, 1968-1981 (2006). https://doi.org/10.1038/sj.cdd.4401898.
Zhaoqing Li et al, "Targeting ferroptosis in breast cancer"; Biomark Res. 2020; 8: 58. Published online Nov. 5, 2020. doi: 10.1186/s40364-020-00230-3.

*Primary Examiner* — Kamal A Saeed
(74) *Attorney, Agent, or Firm* — Nath, Goldberg & Meyer; Richard C. Litman

(57) ABSTRACT

Thiazole tethered organoselenide compounds, a method of synthesizing said compounds, a pharmaceutical composition comprising said compounds and a suitable carrier, and a method of using the compounds. The thiazole tethered organoselenide compounds are identified as being capable of inhibiting 5-lipoxygenase (5-LO).

17 Claims, No Drawings

THIAZOLE TETHERED ORGANOSELENIDES AS 5-LIPOXYGENASE INHIBITORS

BACKGROUND

1. Field

The present disclosure provides thiazole-based organoselenium compounds that are active as 5-lipoxygenase (5-LO) inhibitors.

2. Description of the Related Art

Bronchial asthma (BA), a chronic noncommunicable disease, is a serious global health challenge affecting all ages of people worldwide. In 2019, it accounted for approximately 262 million cases and 455,000 deaths. Recently, Saudi Arabia has witnessed an alarming growth of BA prevalence, particularly among children, which in turn burdens the Saudi healthcare system.

5-Lipoxygenase (5-LO) is a crucial enzyme implicated in the formation of leukotrienes, arachidonic acid, and several mediators of inflammatory and oxidative responses. 5-LO is mostly found in the central nervous system, where its elevated levels are noticed among old people, proposing its role in neurodegeneration. Accordingly, the use of 5-LO inhibitors is considered a promising model for neuroprotective therapy.

It has become clear that 5-LO inhibitors have critical roles in inflammatory responses and are being explored as possible treatments for asthma and respiratory viral infections. Indeed, 5-LO inhibitors can, therefore, be beneficial to reduce COVID-19 patient mortality rate and may help prevent disease progression and severity.

On the other hand, thiazole scaffolds are present in at least eighteen drugs in the market. Furthermore, some experiments on the studied thiazole derivatives have shown a superior activity than the reference drugs, which in turn makes thiazole a versatile pharmacophore in drug discovery. Within this context, different thiazole-based compounds have been developed in the last decade, and assessed for a broad range of pharmacological properties, such as antioxidant, anti-inflammatory, and antiallergic properties.

SUMMARY

The compounds described herein pertain to the field of pharmaceuticals, particularly thiazole-based compounds, the process of synthesis thereof, compositions including these compounds, and the use of the compounds as 5-lipoxygenase (5-LO) inhibitors.

A multitarget-directed therapeutic approach has shown considerable progress in treating different inflammatory disorders where it attains high efficiency by simultaneously hitting various targets, utilizing synergy, and diminishing individual toxicity. Accordingly, the presently disclosed compounds were created during exploration of this therapeutic approach.

In an embodiment, the present subject matter relates to a compound having the formula I:

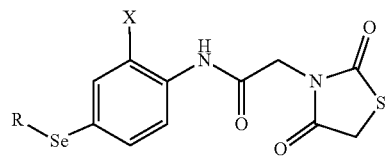

or a pharmaceutically acceptable salt, ester, stereoisomer, or solvate thereof, wherein:

R is selected from the group consisting of

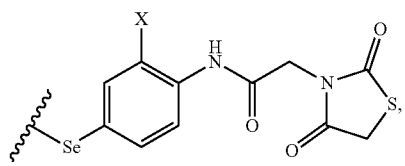

methyl, ethyl, butyl, pentyl, and hexyl; and each X is the same or different and is H or COOMe.

In another embodiment, the present subject matter relates to a compound having the formula I:

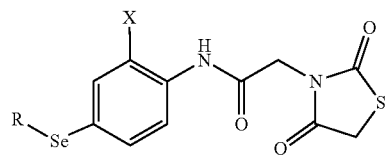

or a pharmaceutically acceptable salt, ester, stereoisomer, or solvate thereof, wherein:

R is methyl, ethyl, butyl, pentyl, and hexyl; and

X is H or COOMe.

In an embodiment, the present subject matter relates to a compound selected from the group consisting of:

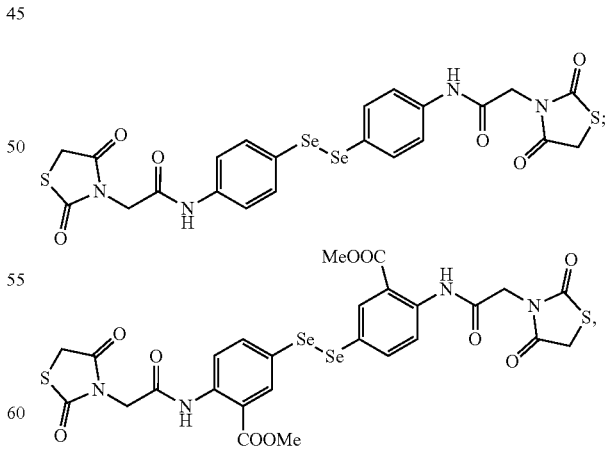

or a pharmaceutically acceptable salt, ester, stereoisomer, or solvate thereof.

In an additional embodiment, the present subject matter relates to a compound selected from the group consisting of:

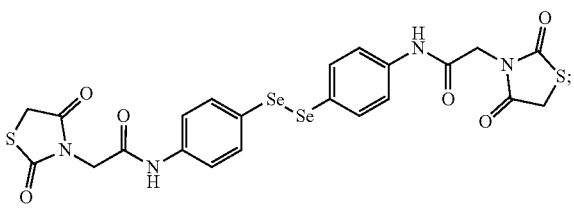 [SMILES: O=C(CN1C(=O)CSC1=O)Nc1ccc([Se][Se]c2ccc(NC(=O)CN3C(=O)CSC3=O)cc2)cc1]

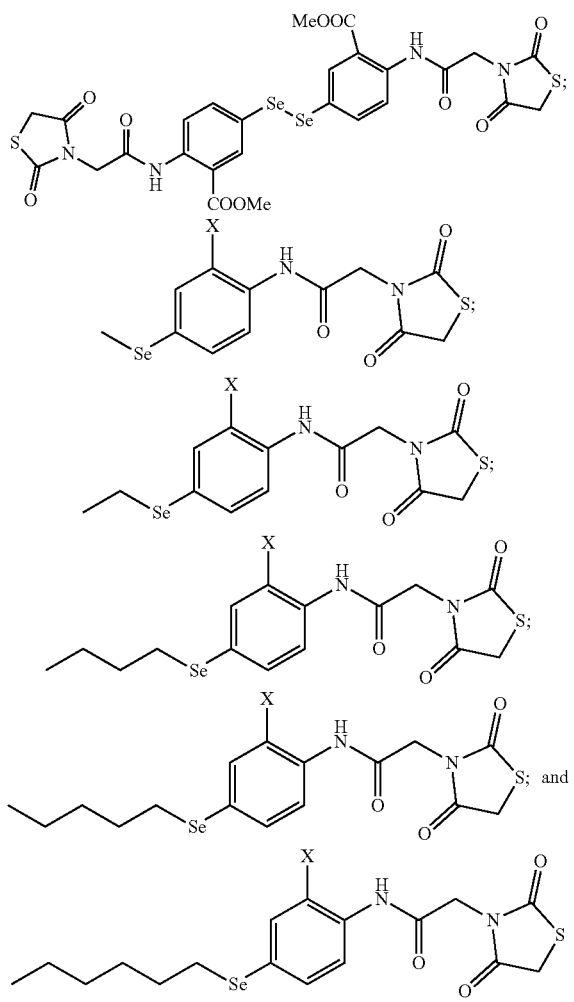

or a pharmaceutically acceptable salt, ester, stereoisomer, or solvate thereof;

wherein X is H or COOMe.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting 5-lipoxygenase in a patient by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "heteroatom" refers to an atom of any element other than carbon or hydrogen and includes, for example, nitrogen, oxygen, silicon, sulfur, phosphorus, and selenium.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as a condition implicated by 5-lipoxygenase.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The compounds described herein pertain to the field of pharmaceuticals, particularly thiazole-based compounds, the process of synthesis thereof, compositions including these compounds, and the use of the compounds as 5-lipoxygenase (5-LO) inhibitors.

In an embodiment, the present subject matter relates to a compound having the formula I:

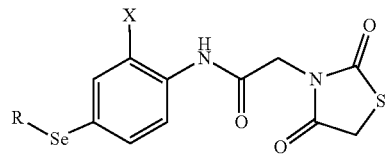

or a pharmaceutically acceptable salt, ester, stereoisomer, or solvate thereof, wherein:
R is selected from the group consisting of

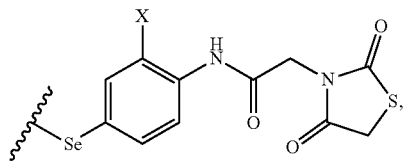

methyl, ethyl, butyl, pentyl, and hexyl; and
each X is the same or different and is H or COOMe.

In one embodiment, each X is H. In an alternative embodiment, each X is COOMe.

In another embodiment, the present subject matter relates to a compound having the formula I:

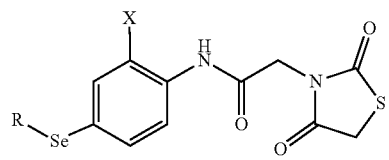

or a pharmaceutically acceptable salt, ester, stereoisomer, or solvate thereof, wherein:
R is methyl, ethyl, butyl, pentyl, and hexyl; and
X is H or COOMe.

In an embodiment, the present subject matter relates to a compound selected from the group consisting of:

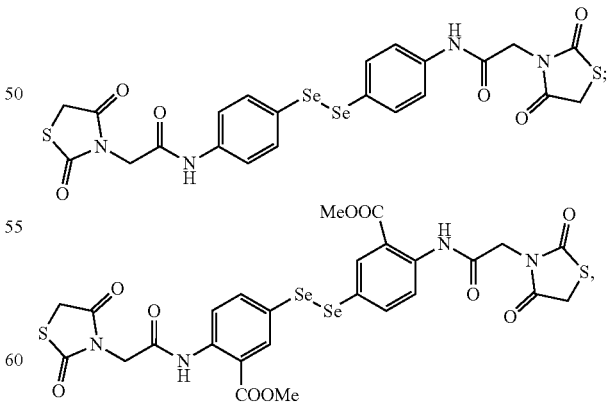

or a pharmaceutically acceptable salt, ester, stereoisomer, or solvate thereof.

In an additional embodiment, the present subject matter relates to a compound selected from the group consisting of:

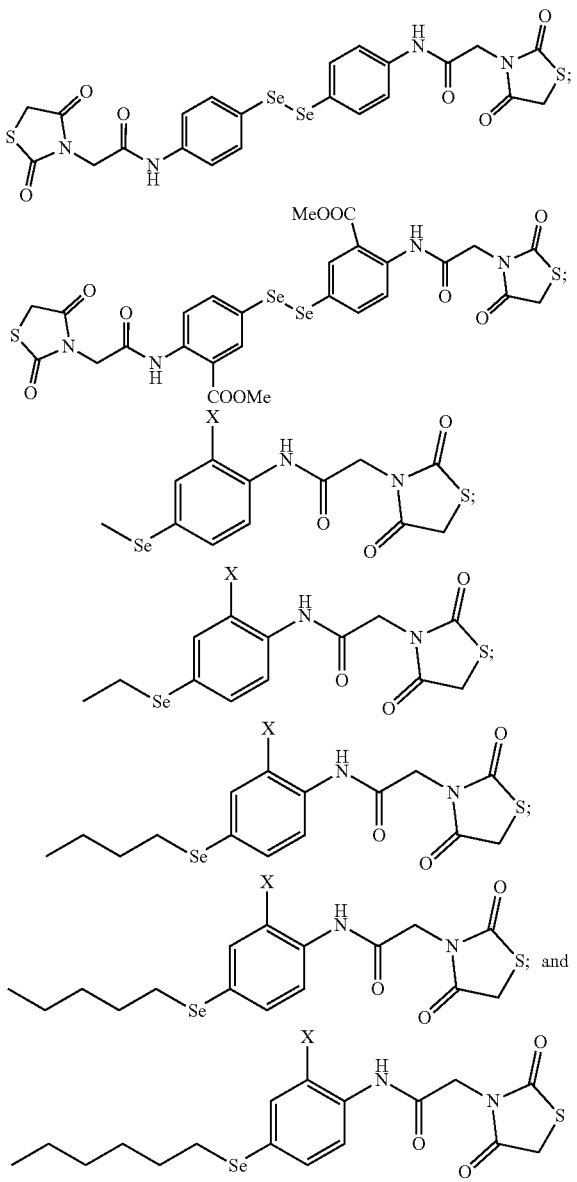

or a pharmaceutically acceptable salt, ester, stereoisomer, or solvate thereof;

wherein X is H or COOMe.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; low molecular weight aliphatic esters such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, and precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via the formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, equimolar amounts of chloroacetic acid thiourea and monochloroacetic acid in water are reacted to obtain 2,4-thiazolidinedione 1. The thiazolidinedione 1 is then reacted with potassium hydroxide in ethanol to obtain a corresponding potassium salt 2. This potassium salt 2 is then reacted with an organoselenium chloro derivative 3 in a nucleophilic substitution reaction to obtain the present thiazole tethered organoselenide 4. The synthetic strategy adopted is illustrated in Scheme 1.

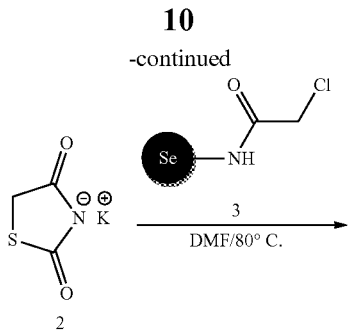

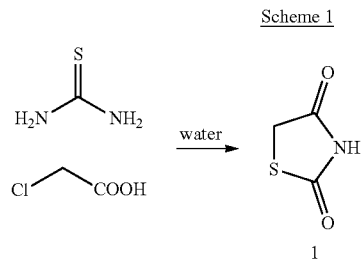

Scheme 1

The organoselenium chloro derivatives 3 useful in this regard can be obtained according to the following Scheme 2.

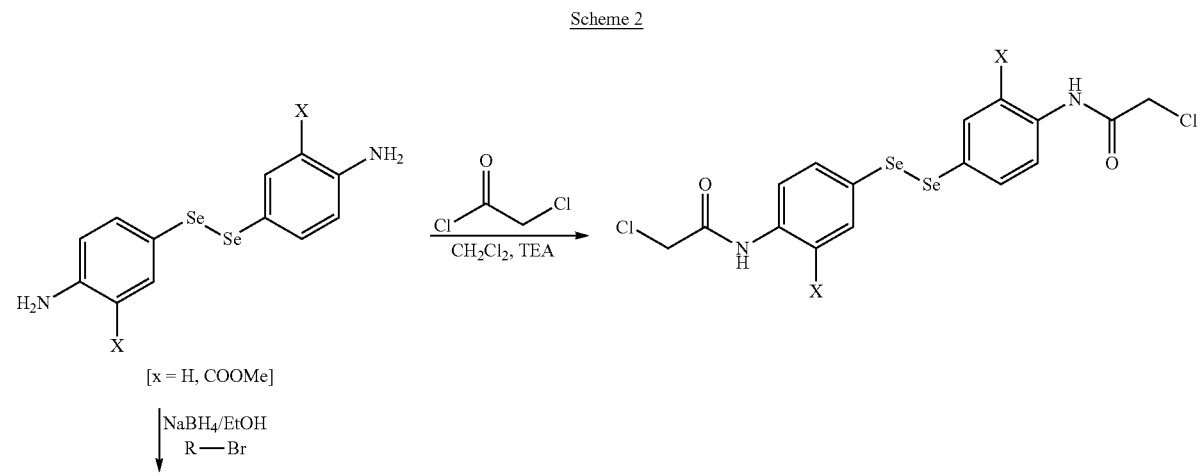

Scheme 2

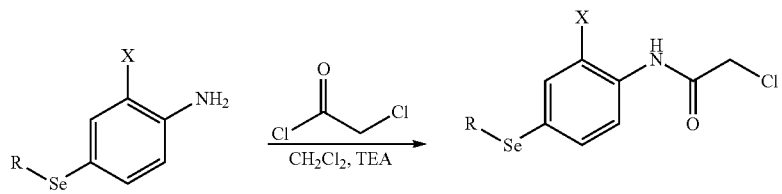

[R = ethyl, butyl, pentyl, hexyl]

In another embodiment, the present subject matter is directed to pharmaceutical compositions comprising a therapeutically effective amount of the compounds as described herein, together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one, two, or more of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment of a condition implicated by 5-lipoxygenase. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for the treatment of a condition implicated by 5-lipoxygenase, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods, and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, nontoxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained-release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable nontoxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained-release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol, or the like. In addition, if desired, the pharmaceutical compositions to be administered may also contain minor amounts of nontoxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compounds contained in such parenteral compositions is highly dependent on the specific nature thereof, as well as the activity of the compound and the needs of the subject. However, percentages of the active ingredient of 0.01% to 10% in solution are employable and will be higher if the composition is a solid, which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds, for example, for the treatment of a condition implicated by 5-lipoxygenase.

In this regard, the present compounds can be considered as 5-lipoxygenase (5-LO) inhibitors. As such, these compounds can be useful in treating a variety of conditions in a patient, including by way of non-limiting example bronchial asthma, a respiratory viral infection, and a combination thereof. Further in this regard, the present compounds may be useful to prevent and/or treat COVID-19 in a patient. Prevention and treatment of COVID-19 as considered herein can include preventing disease progression and/or severity and reducing mortality rate.

In an alternative embodiment, the present compounds can be useful for providing an antioxidant, an anti-inflammatory, and/or an antiallergic effect upon administration to a patient.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one, two, or more of the present compounds are used, or one of the present compounds is used. Similarly, one or more of the present compounds can be used in combination therapy with one or more additional active agents.

It is to be understood that the thiazole tethered organoselenides are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A compound having the formula I:

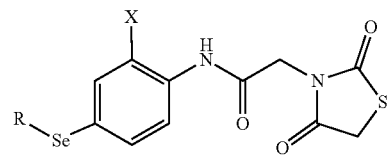

or a pharmaceutically acceptable salt, ester, stereoisomer, or solvate thereof, wherein:
R is selected from the group consisting of

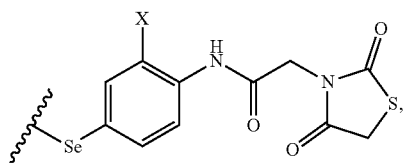

methyl, ethyl, butyl, pentyl, and hexyl; and
each X is the same or different and is H or COOMe.
2. The compound of claim 1, wherein each X is H.
3. The compound of claim 1, wherein each X is COOMe.
4. The compound of claim 1, wherein:
R is methyl, ethyl, butyl, pentyl, and hexyl; and
X is H or COOMe.
5. The compound of claim 1, wherein the compound is selected from the group consisting of:

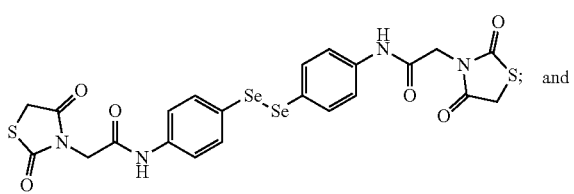

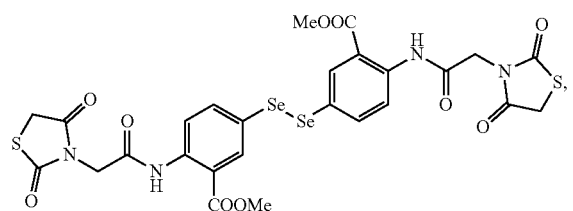

or a pharmaceutically acceptable salt, ester, stereoisomer, or solvate thereof.

6. The compound of claim 1, wherein the compound is selected from the group consisting of:

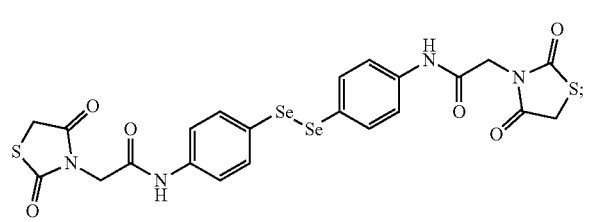

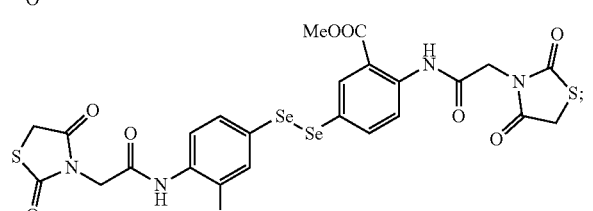

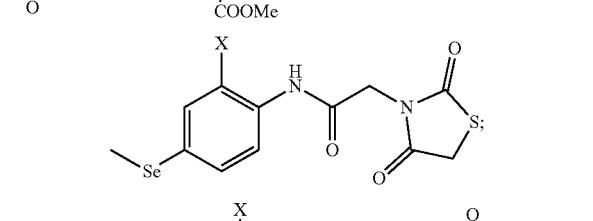

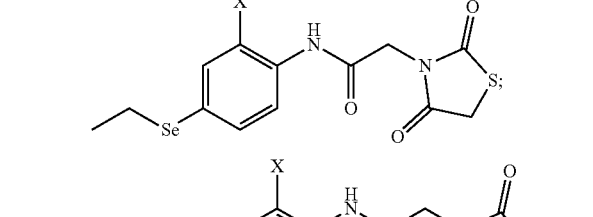

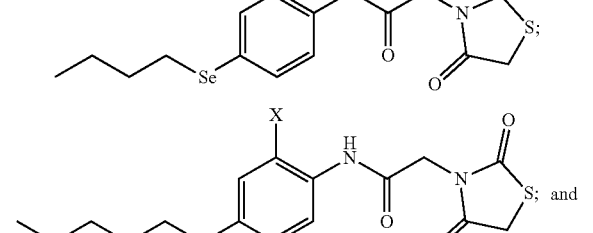

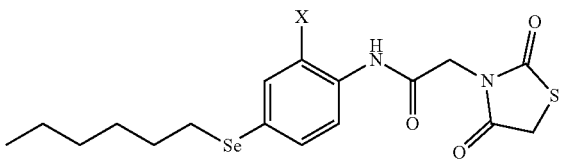

or a pharmaceutically acceptable salt, ester, stereoisomer, or solvate thereof;

wherein X is H or COOMe.

7. A pharmaceutically acceptable composition comprising a therapeutically effective amount of the compound of claim 1 and a pharmaceutically acceptable carrier.

8. A method of inhibiting 5-lipoxygenase (5-LO) activity in a patient, comprising administering to a patient in need thereof a therapeutically effective amount of the compound of claim 1.

9. The method of inhibiting 5-lipoxygenase (5-LO) activity in a patient of claim 8, wherein administration of the compound to the patient treats asthma, a respiratory viral infection, or a combination thereof in the patient.

10. A method of treating asthma in a patient, comprising administering to a patient in need thereof a therapeutically effective amount of the compound of claim 1.

11. A method of treating a respiratory viral infection in a patient, comprising administering to a patient in need thereof a therapeutically effective amount of the compound of claim 1.

12. The method of treating a respiratory viral infection in a patient of claim 11, wherein the respiratory viral infection is caused by COVID-19.

13. The method of treating a respiratory viral infection in a patient of claim 12, wherein the administration of the compound reduces patient mortality rate, prevents COVID-19 progression, or prevents COVID-19 severity.

14. A compound selected from the group consisting of:

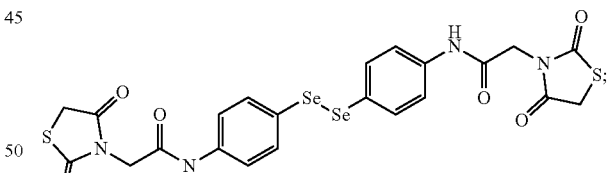

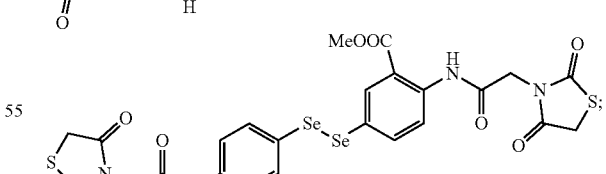

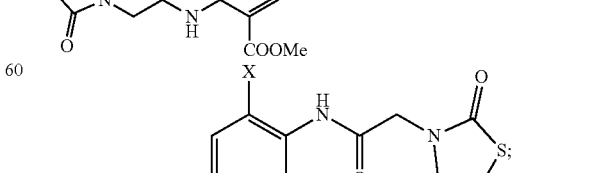

-continued

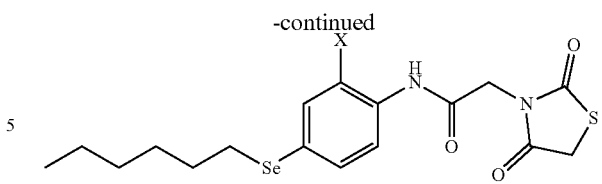

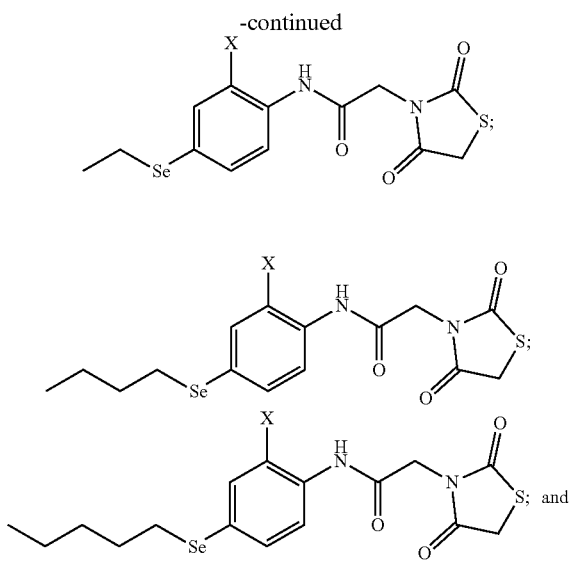

or a pharmaceutically acceptable salt, ester, stereoisomer, or solvate thereof;

wherein X is H or COOMe.

15. A pharmaceutically acceptable composition comprising a therapeutically effective amount of the compound of claim 14 and a pharmaceutically acceptable carrier.

16. A method of inhibiting 5-lipoxygenase (5-LO) activity in a patient, comprising administering to a patient in need thereof a therapeutically effective amount of the compound of claim 14.

17. The method of inhibiting 5-lipoxygenase (5-LO) activity in a patient of claim 16, wherein administration of the compound to the patient treats asthma, a respiratory viral infection, or a combination thereof in the patient.

* * * * *

UNITED STATES PATENT AND TRADEMARK OFFICE
CERTIFICATE OF CORRECTION

| | |
|---|---|
| PATENT NO. | : 11,999,708 B1 |
| APPLICATION NO. | : 18/590133 |
| DATED | : June 4, 2024 |
| INVENTOR(S) | : Saad Shaaban et al. |

It is certified that error appears in the above-identified patent and that said Letters Patent is hereby corrected as shown below:

On the Title Page

Item (72) Inventors, please delete the Inventor city for Inventors 3 and 4 "MOHAMED ALAA MOHAMED, Al-Ahsa, (SA)" and "ABEER M. ASHMAWY, Al-Ahsa, (SA)" and replace with "MOHAMED ALAA MOHAMED, Buffalo, (NY)" and "ABEER M. ASHMAWY, Cairo, (EG)"

Signed and Sealed this
Tenth Day of December, 2024

Katherine Kelly Vidal
*Director of the United States Patent and Trademark Office*